US012582682B2

(12) United States Patent
Navarro Lopez et al.

(10) Patent No.: US 12,582,682 B2
(45) Date of Patent: Mar. 24, 2026

(54) PROBIOTIC COMPOSITIONS FOR THE TREATMENT OF ACNE

(71) Applicant: Bionou Research S.L., Sant Joan d'Alacant (ES)

(72) Inventors: Vincente Navarro Lopez, Sant Joan d'Alacant (ES); Laura Navarro Moratalla, Sant Joan d'Alacant (ES)

( * ) Notice: Subject to any disclaimer, the term of this patent is extended or adjusted under 35 U.S.C. 154(b) by 354 days.

(21) Appl. No.: 18/025,944

(22) PCT Filed: Sep. 14, 2021

(86) PCT No.: PCT/EP2021/075219
§ 371 (c)(1),
(2) Date: Mar. 13, 2023

(87) PCT Pub. No.: WO2022/053711
PCT Pub. Date: Mar. 17, 2022

(65) Prior Publication Data
US 2024/0033308 A1 Feb. 1, 2024

(30) Foreign Application Priority Data
Sep. 14, 2020 (EP) .................................... 20382805

(51) Int. Cl.
| | |
|---|---|
| *A61K 35/747* | (2015.01) |
| *A61K 9/48* | (2006.01) |
| *A61K 35/748* | (2015.01) |
| *A61P 17/10* | (2006.01) |
| *A61K 35/00* | (2006.01) |

(52) U.S. Cl.
CPC .......... *A61K 35/747* (2013.01); *A61K 9/4825* (2013.01); *A61K 9/485* (2013.01); *A61K 9/4858* (2013.01); *A61K 9/4866* (2013.01); *A61K 35/748* (2013.01); *A61P 17/10* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 8,808,706 B2 | 8/2014 | Duncan et al. |
| 9,498,504 B2 | 11/2016 | Keimes et al. |
| 2019/0350988 A1 | 11/2019 | Henn et al. |

FOREIGN PATENT DOCUMENTS

| | | |
|---|---|---|
| CN | 101928743 | 12/2010 |
| CN | 109315769 | 2/2019 |
| EP | 1975257 | 10/2008 |
| EP | 3222282 | 9/2017 |
| KR | 201550142764 | 12/2015 |
| RU | 2656152 | 5/2018 |

| | | |
|---|---|---|
| WO | 2006047830 | 5/2006 |
| WO | 2013153358 | 10/2013 |
| WO | 2015059690 | 4/2015 |

OTHER PUBLICATIONS

Philippe Marteau. "Evidence of probiotic strain specificity makes extrapolation of results impossible from a train to another, even from the same species". Annals or Gastroenterology and Hepatology 2011, pp. 1-3.*
Guarner, Francisco, et al., "Probiotics and Prebiotics", World Gastroenterology Organization, May 2008, pp. 1-22.
Huili, Wang, et al., "Proteomic Analysis and qRT-PCR Verification of Temperature Response to Arthrospira (Spirulina) Platensis", PLOS One, Dec. 2013, vol. 8, Issue 12, pp. 1-23.
International Search Report based on co-pending International Application No. PCT/EP2021/075219, dated Mar. 17, 2022—pp. 1-6.
Written Opinion based on co-pending International Application No. PCT/EP2021/075219, dated Mar. 17, 2022—pp. 1-13.
Bowe, Whitney P., et al., "Acne Vulgaris, Probiotics and the Gut-Brain-Skin Axis—Back to the Future?", Bowe and Logan Gut Pathogens, Jan. 31, 2011, vol. 3, No. 1, pp. 1-11.
Siver, Robert H., "Lactobacillus for the Control of Acne", The Journal of the Medical Society of New Jersey, Feb. 1961, vol. 38, No. 1, pp. 52-53.
Jung, Gordon W., et al., "Prospective, Randomized, Open-Label Trial Comparing the Safety, Efficacy, and Tolerability of an Acne Treatment Regimen with and without a Probiotic Supplement and Minocycline in Subjects with Mild to Moderate Acne", Journal of Cutaneous Medicine and Surgery, Mar./Apr. 2013, vol. 17, No. 2, pp. 114-122.
Hacini-Rachinel, Feriel, et al., "Oral Probiotic Control Skin Inflammation by Acting on Both Effector and Regulatory T Cells", PLoS One, Mar. 2009, vol. 4, Issue 3, pp. 1-9.
Livingston, Megan, et al., "Gut Commensal Lactobacillus Reuteri 100-23 Stimulates an Immunoregulatory Response", Immunology and Cell Biology, Sep. 29, 2009, vol. 88, pp. 99-102.
Gueniche, A., et al., "Randomised Double-Blind Placebo-Controlled Study of the Effect of Lactobacillus Paracasei NCC 2461 on Skin Reactivity", Beneficial Microbes, Jan. 3, 2013, vol. 5, pp. 137-145.
Benyacoub, J., et al., "Immune Modulation Property of Lactobacillus Paracasei NCC2461 (ST11) Strain and Impact on Skin Defences", Beneficial Microbes, Feb. 14, 2013, vol. 5, pp. 129-136.
Fabbrocini, G., et al., "Supplementation with Lactobacillus Rhamnosus SP1 Normalises Skin Expresion of Genes Implicated in Insulin Signalling and Improves Adult Acne", Beneficial Microbes, May 16, 2016, vol. 7, No. 5, pp. 625-630.
Anonymous: "AY675254 Lactobacillus Rhamnosus Strain LR2 16S Ribosomal RNA Gene, Complete Sequence", GenBank, Oct. 9, 2004, p. 1.
Bionou Research, et al., "NCT03878238 A Pilot Study to Evaluate the Effect of a Probiotic Mixture of Acne", ClinicalTrials.gov, Mar. 15, 2019, pp. 1-3 (Retrieved from the Internet: URL: https://clinicaltrials.gov/ct2/show/NCT03878238).

* cited by examiner

*Primary Examiner* — Vera Afremova
(74) *Attorney, Agent, or Firm* — McCarter & English, LLC

(57) ABSTRACT
Probiotic compositions are provided in the present invention that comprise bacterial strains *L. rhamnosus* CECT 30031 and bacterial strain *Arthrospira platensis* (*Spirulina paraca*). The disclosed probiotic compositions are useful in the treatment of acne.

17 Claims, 3 Drawing Sheets
Specification includes a Sequence Listing.

GAGS INDEX

INFLAMED ACNE LESIONS

PROBIOTIC COMPOSITIONS FOR THE TREATMENT OF ACNE

TECHNICAL FIELD

Probiotic compositions are provided that are useful in the treatment of acne.

BACKGROUND OF THE INVENTION

The term probiotic has been defined as "living microorganisms which, when consumed in adequate amounts, confer a health effect on the host" (World Health Organization and Food and Agriculture Organization of the United Nations, 2001). The earliest report on probiotics dates back to 1907, when Elie Metchnikoff described a correlation between the ingestion of lactic acid-producing bacteria in yogurt and enhanced longevity. During the past few decades, there has been renewed interest in probiotics not only regarding digestive health, but also in the management of inflammatory diseases.

Oral probiotics have been shown to improve insulin sensitivity in animal models as well as regulate the release of inflammatory cytokines in the skin through their interaction with gut-associated lymphoid tissue (Hacini-Rachinel G., Gheit H., Le Luduec J. B., Dif F., Nancey S., Kaiserlian D. Oral probiotic control skin inflammation by acting on both effector and regulatory T cells. PLoS One. 2009; 4:e4903). In fact, the gut-brain-skin axis suggests a mechanism that links gastrointestinal health, influenced by interactions with oral probiotics, to the health and well-being of the skin (Bowe W. P., Logan A. C. Acne vulgaris, probiotics and the gut-brain-skin axis: back to the future? Gut Pathog. 2011; 3:1). In this sense, several strains of *Lactobacillus* have been shown to have systemic anti-inflammatory effects. Studies have shown that *Lactobacillus reuteri* induces systemic anti-inflammatory cytokines, such as interleukin (IL)-10. Soluble factors from *L. reuteri* inhibit production of pro-inflammatory cytokines and culture supernatants of murine-derived *L. reuteri* 6798 inhibit tumor necrosis factor (TNF) production of activated macrophages (Livingston M., Loach D., Wilson M., Tannock G. W., Baird M. Gut commensal *Lactobacillus reuteri* 100-23 stimulates an immunoregulatory response. Immunol Cell Biol. 2009; 88:99-102).

Several strains of *Lactobacillus* also demonstrate anti-inflammatory properties. The addition of *Lactobacillus paracasei* NCC2461 has been shown to inhibit neutrogenic inflammation in a skin model, and the addition of *L. paracasei* NCC2461 to lymphocyte culture has been shown to strongly inhibit the proliferative activity of CD-4+ T-cells in a dose-dependent manner and to induce the anti-inflammatory cytokines IL-10 and TGF-beta. Mice who consumed the probiotic for 7 days demonstrated a significantly higher antibody response and in vivo T-cell-mediated immune response, indicating *L. paracasei* affects both B- and T-cell function. Similarly, mice treated with *Lactobacillus casei* had an increased ability to produce IL-10 and promote T-regulatory cell function. An increase in T-regulatory cells suggests that this probiotic may help to balance the immune system's response to stimuli (Hacini-Rachinel G., Gheit H., Le Luduec J. B., Dif F., Nancey S., Kaiserlian D. Oral probiotic control skin inflammation by acting on both effector and regulatory T cells. PLoS One. 2009; 4:e4903). Consequently, certain probiotic strains may potentially boost appropriate immune responses, for example to a harmful pathogenic threat, while dampening the unnecessary immune responses seen in chronic inflammatory states.

Disruption of skin barrier function is a known side effect of many acne medications including topical retinoids and benzoyl peroxide. The irritation, stinging, and dryness resulting from these medications can negatively impact compliance with an acne regimen. Rosacea and atopic dermatitis are other skin conditions in which the skin barrier is impaired, and symptoms improve when the skin barrier is strengthened. Oral ingestion of certain probiotic strains has been shown to improve the skin barrier and affect skin hydration and transepidermal water loss. In fact, Gueniche et al. (2014) (Gueniche A., Phillippe D., Bastien P., Reuteler G., Blum S., Castiel-Higounenc I. Randomised double-blind placebo-controlled study of the effect of *Lactobacillus paracasei* NCC 2461 on skin reactivity. Benef Microbes. 2014; 5:137-145) studied the effects of oral supplementation with *L. paracasei* NCC2461 versus placebo for healthy female volunteers in a randomized placebo-controlled clinical trial. A capsaicin test was used to monitor skin sensitivity, while trans-epidermal water loss and dermatological assessments were utilized to measure skin barrier function. Both skin sensitivity and skin barrier function improved in the probiotic group. The probiotic group also showed increases in the serum concentration of TGF-beta after 29 days compared to no increase in the placebo group. TGF-beta has been shown to play a significant role in skin integrity.

Thus, overall, probiotics modulate the development of the immune system, often shifting the immune response toward regulatory and anti-inflammatory conditions. This ability of probiotics to modify chronic inflammatory states suggests that probiotics may have a role in treating chronic inflammatory conditions, ranging from inflammatory bowel disease to reactive airway disease to acne, rosacea, atopic dermatitis, and photoaging (Benyacoub J., Bosco N., Blanchard C., Demont A., Phillippe D., Castiel-Higounenc I. Immune modulation property of *Lactobacillus paracasei* NCC2461 (ST11) strain and impact on skin defenses. Benef Microbes. 2014; 5:129-136). In this sense, evidences in probiotic interventions for acne in human studies are summarized below in table 1.

TABLE 1

| Evidence of beneficial probiotic interventions in acne vulgaris. Adapted from: (11) | | | | |
|---|---|---|---|---|
| Author | Study design | Oral probiotic | Clinical response | Proposed mechanism |
| Silver RH. *Lactobacillus* for the control of acne. J Med Soc New Jersey. 1961; 59: 52-53. | Intervention group only; 300 subjects with acne | *L. acidophilus* and *L. bulgaricus** (probiotic × 8 days, 2-weeks washout, then re-introduction × | Clinical improvement in 80% of patients, particularly those with | Mechanism not established |

TABLE 1-continued

Evidence of beneficial probiotic interventions in acne vulgaris. Adapted from: (11)

| Author | Study design | Oral probiotic | Clinical response | Proposed mechanism |
|---|---|---|---|---|
| | | 8 days) | inflammatory acne | |
| Jung Tse JE, Guiha I, Rao J. Prospective, randomized, open-label trial comparing the safety, efficacy, and tolerability of an acne treatment regimen with and without a probiotic supplement and minocycline in subjects with mild to moderate acne. J Cutan Med Surg. 2013; 17(2): 114-122. doi: 10.2310/7750.2012.12026 | Randomized, controlled, open-label; 45 females with acne | L. acidophilus (NAS), LB-51*, B. bifidum, (5 × 109, 5 × 109, 20 × 109 CFU 2x/d × 12 weeks | Significant $\downarrow$ in number of acne lesions with using probiotic together with Abs than Abs alone | Synergistic anti-inflammatory effect |
| Fabbrocini G, Bertona M, Picazo Ó, Pareja-Galeano H, Monfrecola G, Emanuele E. Supplementation with Lactobacillus rhamnosus SP1 normalises skin expression of genes implicated in insulin signalling and improves adult acne. Benef Microbes. 2016; 7(5): 625-630. doi: 10.3920/BM2016.0089 | Randomized, double-blind, placebo-controlled; 20 adults with acne | L. rhamnosus SP1 (3 × 109 CFU/d (75 mg/d) × 12 weeks) | Improved appearance of adult acne | Normalized skin expression of genes involved in insulin signaling $\downarrow$ IGF-1* expression, $\uparrow$ FOXO1) |

However, there is still a need to provide further probiotic compositions that deliver a significant improvement in the overall treatment of acne, in particular a significant improvement according to well-known and accepted grading systems such as the Global Acne Grading system (GAGS) or the AGSS (Acne Global Severity Scale).

DESCRIPTION OF THE INVENTION

Figure 1:
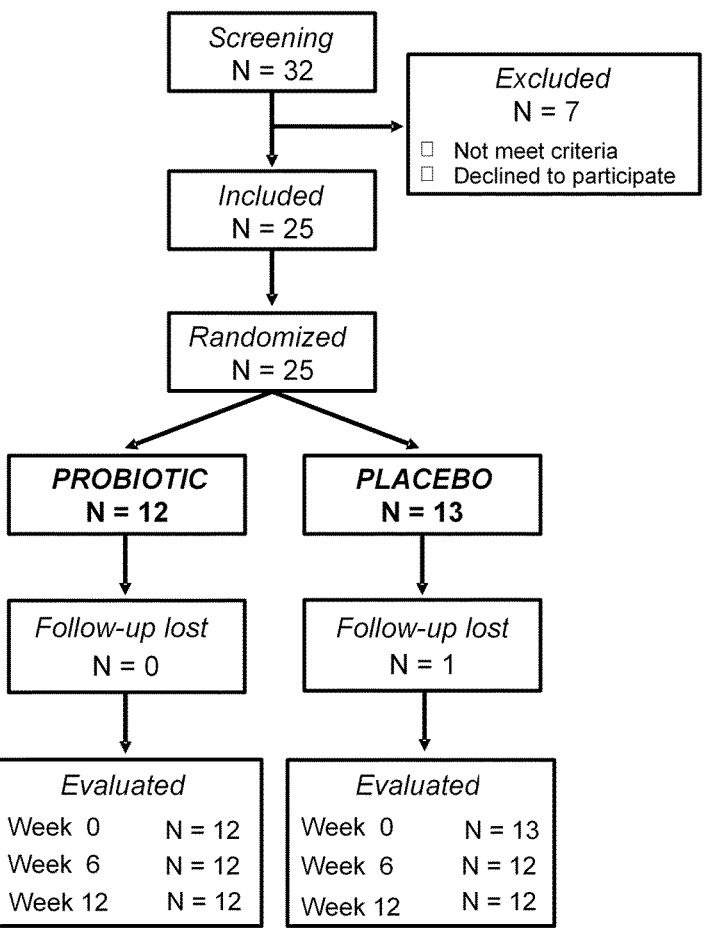
FIG. 1. Consort diagram used in the probiotic blend study of example 1.

In the present invention, we have tested a novel Malto-dextrin-based formula named Bths-03 containing a mixture of two strains comprising at least $1\times10^9$ cfu (colony forming units) per gram (see example 1). In particular, said mixture of two strains comprised bacterial strain Lactobacillus rhamnosus CECT 30031 and the bacterial strain Arthrospira platensis BEA_IDA_0074B (also referred to as Spirulina paraca (S. paraca)).

L. rhamnosus is a bacterium commonly used as a probiotic, found mostly in yogurt and other dairy products, including infant formula. The scientific classification of L. rhamnosus is: Domain: Bacteria Phylum: Firmicutes Class: Bacilli Order: Lactobacillales, Family: Lactobacillaceae, Genus: Lactobacillus, Species: Lactobacillus rhamnosus.

Arthrospira platensis is an aquatic, prokaryotic filamentous gram negative, included in the Domain: Bacteria; Phylum: Cyanobacteria; Class: Cyanophyceae; Genera: Cyanobacteria, which is often classified as a blue/green microalga although it is a prokaryotic bacterial microorganism. The common name of its commercialized biomass is "Spirulina" which production makes this microorganism to be the most cultivated worldwide. Arthrospira platensis is therefore also known under the name of Spirulina paraca (S. paraca).

By using the above mixture, and as illustrated in example 1 accompanying the present specification, we conducted a pilot study which included patients with moderate acne vulgaris and who were prescribed treatment with topical and systemic antibiotics. As shown therein, the percentage of response in the probiotic group according to the Global Acne Grading system (GAGS) was 61.8% and 35.4% in the placebo group. This difference in absolute value of approximately 26 points in the percentage of improvement was considered clinically relevant and with statistical significance. A further clinically important variable that was measured was the AGSS (Acne Global Severity Scale) variable. Differences between groups were also observed for this variable, in particular, in the probiotic group the index improved by 58% and 33% in the placebo group. As regards, the variable "number of inflammatory lesions", this variable showed differences between the two groups of clinical and statistical relevance with an improvement in the probiotic group in 76.5% of the lesions whereas in the placebo group an improvement was only shown in 23.78% of the lesions. This last referred variable was the one that experienced the greatest improvement during the treatment in favor of the group treated with the probiotic blend. In addition, the subjective impression of the patients showed an improvement of 29.58% in the probiotic group at the end of treatment while in the placebo group this variable showed a 4.75% of improvement. Furthermore, all the main variables (primary and secondary) showed more favorable scores in the probiotic group when comparing the data with those of the placebo group, with some of them of important clinical relevance and statistical significance. Adherence to treatment was 90% in both groups while the number of side effects described was low and not attributable to the treatment used in the study.

Based on these results, we can conclude that the present invention provides a novel and improved treatment of acne with a probiotic composition comprising the combination of at least two strains, in particular, bacterial strains pertaining to the species *L. rhamnosus* and pertaining to the species *Arthrospira platensis* (*Spirulina paraca*). More particularly, the present invention refers to the combination of at least the bacterial strain *Lactobacillus rhamnosus* named AcnéPro-Bths, deposited by Bioithas (03080 Sant Vicent del Raspeig, Alicante, Spain) in the Spanish Type culture Collection (CECT) (C/Catedrático Agustin Escardino, 9. 46980 Paterna (Valencia). Spain) under accession number CECT 30031, on Dec. 3, 2019 (from hereinafter referred to throughout the present specification as *L. rhamnosus* CECT 30031); and the *Arthrospira platensis* strain named SPF-bioithas 001, deposited by Bioithas (03080 Sant Vicent del Raspeig, Alicante, Spain) in the Banco Español de Algas (Muelle de Taliarte, s/n 35214—Telde Gran Canaria—Spain) under accession number BEA_IDA_0074B, on Oct. 25, 2019, (from hereinafter referred to throughout the present specification as *S. paraca* BEA_IDA_0074B or *Arthrospira platensis* BEA_IDA_0074B).

Furthermore, and as illustrated in the accompanying examples, prior to the study or trial described in example 1, each of strains *L. rhamnosus* CECT 30031 and *S. paraca* BEA_IDA_0074B were evaluated separately for the treatment of acne vulgaris. For such purpose a small pilot study was performed with five patients in each one of a three-branch study using only *L. rhamnosus* CECT 30031, only *S. paraca* BEA_IDA_0074B or CECT 30031 and *S. paraca* BEA_IDA_0074B. The results of this study are provided in example 2, where it is therein reflected how the effect is markedly potentiated and thus significantly improved when both strains are used in combination compared with the effect of each of the strains separately.

Moreover, also prior to the trial described in example 1, a probiotic composition comprising the *S. paraca* BEA_IDA_0074B strain was specifically compared with a probiotic composition containing the known strain (Strain 1. *L. rhamnosus* SP1) disclosed in: "Fabbrocini G, Bertona M, Picazo Ó, Pareja-Galeano H, Monfrecola G, Emanuele E. Supplementation with *Lactobacillus rhamnosus* SP1 normalises skin expression of genes implicated in insulin signaling and improves adult acne. Benef Microbes. 2016; 7 (5): 625-630. doi: 10.3920/BM2016.0089". Such known strain was considered in the prior art as effective for the treatment of acne vulgaris (see table 1 above). The results are shown in example 3.

It is thus clear from the results shown in example 3 in relation to the *L. rhamnosus* SP1 strain and from the data shown in example 2 referring to *L. rhamnosus* CECT 30031 (both when used individually), that the *L. rhamnosus* CECT 30031 strain is significantly more effective for the treatment of acne vulgaris than the *L. rhamnosus* SP1 strain. Moreover, based on the results shown in examples 1 to 3, it is also clear that the anti-acne effect is remarkably potentiated when

*L. rhamnosus* CECT 30031 is used in combination with the *S. paraca* BEA_IDA_0074B strain.

Thus, a first aspect of the invention refers to a probiotic composition which comprises the combination of strains *L. rhamnosus* CECT 30031 and *S. paraca* BEA_IDA_0074B.

In the present invention the term "probiotic composition", as used in any of the above aspects, is understood as a composition comprising at least one microorganism which, when ingested, interacts with the individual's metabolism and produces a beneficial effect in it. In the present invention, the probiotic composition thus comprises at least the combination of microorganisms *L. rhamnosus* CECT 30031 and *S. paraca* BEA_IDA_0074B.

A second aspect of the present invention refers to probiotic compositions of the first aspect of the invention, for use in the treatment and/or prevention of acne (particularly in a method of easing, reducing, treating and/or preventing acne), in particular of acne vulgaris, more particularly in the prevention or treatment of comedones (e.g. reducing the number of comedones and/or preventing comedones from getting worse), in a subject or individual in need thereof.

A third aspect of the invention refers to a probiotic composition comprising *Arthrospira platensis* (*S. paraca*) strain deposited in the Banco Español de Algas under accession number BEA_IDA_0074B for use in a method of easing, reducing, treating and/or preventing acne, in particular of acne vulgaris, more particularly in easing, reducing, treating and/or preventing comedones, in a subject, preferably a human subject, in need thereof.

A fourth aspect of the invention refers to a probiotic composition comprising *Lactobacillus rhamnosus* strain deposited under the Budapest treaty in the Spanish Type culture Collection (CECT) under accession number CECT 30031 for use in a method of easing, reducing, treating and/or preventing acne, in particular of acne vulgaris, more particularly in easing, reducing, treating and/or preventing comedones, in a subject, preferably a human subject, in need thereof.

In a preferred embodiment of the second, third and fourth aspect of the invention the acne is selected from the group consisting of Acne vulgaris, Acne rosacea, Acne conglobate, Acne fulminans, Gram-negative folliculitis, and Pyoderma Faciale, preferably wherein the acne is Acne vulgaris.

In another preferred embodiment of the second, third and fourth aspect of the invention the probiotic composition is administered orally to the subject.

Other aspects of the invention refer to the compositions herein provided for use in the treatment and/or prevention of diseases characterized by the overproduction of sebum, in particular those that block the pilosebaceous unit that form comedones. Another aspect refers to the compositions herein provided for use in clearing the skin, particularly in the case of oily skin or acne-prone skin.

In the present invention the term "subject" is equivalent to the term "individual", so both terms can be used interchangeably herein. "Subject" means, in addition to any individual, any animal belonging to any species. Examples of subjects include, but are not limited to, animals of commercial interest such as birds (hens, ostriches, chicks, geese, partridges, etc.), rabbits, hares, pets (dogs, cats, etc.), sheep, goat cattle (goats, etc.), swine (boars, pigs, etc.), equine livestock (horses, ponies, etc.), cattle (bulls, cows, oxen, etc.); animals of hunting interest, such as stags, deer, reindeer, etc.; and humans. However, in a particular embodiment, the subject is a mammal, particularly the mammal is a human being of any race, sex or age.

In the present invention the term "prevention" means to avoid occurrence of the disease or pathological condition in an individual, particularly when the individual has predisposition for the pathological condition but has not yet been diagnosed. In a preferred embodiment of the present invention, the disease or pathological condition is "acne".

In the present invention, the term "treat" or "treatment" comprises inhibiting the disease or pathological condition, i.e., stopping its development; relieving the disease or pathological condition, i.e., causing regression of the disease or pathological condition; relieving or reducing at least one of the symptoms or signs of the disease or pathological condition; and/or stabilizing the disease or pathological condition in an individual. In a preferred embodiment of the present invention, the disease or pathological condition is "acne".

In the context of the present invention, it is herein noted that the term "acne" shall be understood as a disease of the sebaceous hair follicles, often called pores. At the base of each hair follicle is a gland called the sebaceous gland, which produces sebum. Sebum is an oily substance that keeps the skin moist and pliable, which under normal circumstances travels along the hair follicle to the surface of the skin. A blemish begins approximately 2-3 weeks before it appears on the skin's surface. As the skin renews itself, the old cells die and slough off. When cells are shed unevenly and clump together with the sebum it forms a plug. Sebum which normally drains to the surface gets blocked and bacteria begin to grow. The rapid growth of the bacteria in combination with the accumulated sebum cause the follicle to enlarge and result in a mild form of acne called comedones, which are non-inflammatory. Both whiteheads and blackheads start out as a "microcomedone" and then become skin blemishes called comedones, either a whitehead or a blackhead. Acne is trapped sebum and bacteria (*Propionibacterium acnes*) growing in a plugged follicle. Sebaceous glands are most numerous on the face, chest, back, neck and scalp; consequently, these are the most common sites of acne. The most common factors that caused acne are hormones, increased sebum production, bacteria (*Propionibacterium acnes*), systemic and local inflammation and changes inside of the hair follicle. Acne may progress to an inflammatory type of acne lesions that are red in color called papules, pustules and nodules.

As used in the present invention, the term acne is not limited to any specific type as there are many types of acne, ranging in severity from mild to severely disfiguring. In particular, the term "acne" as used in the present invention refers to any type of acne, in particular those selected from the list consisting of Acne vulgaris, Acne rosacea, Acne conglobate, Acne fulminans, Gram-negative folliculitis, and Pyoderma Faciale. Particularly the type of acne is Acne vulgaris.

Acne vulgaris is the most common form of acne which includes several types of pimples. These acne lesions include blackheads, whiteheads, papules, pustules, nodules and cysts. Mild to moderate acne vulgaris is characterized by whiteheads, blackheads, papules, and pustules. A whitehead is formed when a pore is completely blocked, trapping sebum, bacteria, and dead skin cells below the skin surface causing a white appearance on the surface. Whiteheads are normally quicker in life cycle than blackheads. A blackhead is formed when a pore is only partially blocked, allowing some of the trapped sebum, bacteria, and dead skin cells to drain to the surface slowly. The black color is due to a reaction of the skin's own pigment, melanin, reacting with the oxygen in the air. A blackhead tends to be a stable structure. Blackheads can often take a long time to clear because the contents very slowly drain to the surface. Papules are small, red, tender bumps with no head. Papules are the earliest stage in the development of what are normally considered the typical "pimple". Papules are an intermediate in the progression of acne between the non-inflammatory and inflammatory stages. Pustules are similar to whiteheads, but are inflamed, and appear as a red circle with a white or yellow center.

Severe acne vulgaris is characterized by nodules and cysts. Nodular acne consists of acne spots which are much larger, can be quite painful, and can sometimes last for months. Nodules are large, hard bumps under the skin's surface. Scarring is common with nodules. An acne cyst can appear similar to a nodule, but is pus-filled, and can been described as having a diameter of 5 mm or more across. They can be painful, and scarring is common with cystic acne.

Acne rosacea can look similar to the aforementioned acne vulgaris, and the two types of acne are sometimes confused for one another. Rosacea affects millions of people, most of whom are over the age of 30. It appears as a red rash which is normally confined to the cheeks, nose, forehead and chin. The redness is often accompanied by bumps, pimples, and skin blemishes. Blood vessels may also become more visible on the skin. Blackheads are not a part of rosacea. It is more prevalent in women, but often more severe when found in men. Left untreated, it can cause swelling of the nose and the growth of excess tissue, a condition called rhinophyma.

Acne conglobata is the most severe form of acne vulgaris and is more common in males. It is characterized by numerous large lesions, which are sometimes interconnected, along with widespread blackheads. It can cause severe, irrevocable damage to the skin, and disfiguring scarring. It is found on the face, chest, back, buttocks, upper arms, and thighs. The age of onset for acne conglobata is usually between 18 and 30 years, and the condition can stay active for many years.

Acne fulminans is an abrupt onset of acne conglobata which normally afflicts young men. Symptoms of severe nodulocystic, often ulcerating acne are apparent. As with acne conglobata, extreme, disfiguring scarring is common. Acne fulminans is unique in that it also includes a fever and aching of the joints.

Gram-negative folliculitis is a bacterial infection characterized by pustules and cysts, possibly occurring as a complication resulting from a long-term antibiotic treatment of acne vulgaris. It is a rare condition, and prevalence in males versus females is unknown.

Pyoderma Faciale is severe facial acne affects only females, usually between the ages of 20 to 40 years old, and is characterized by painful large nodules, pustules and sores which may leave scarring. It begins abruptly and may occur on the skin of a woman who has never had acne before. It is confined to the face, and usually does not last longer than one year, but can wreak havoc in a very short time.

It is noted that the present invention also contemplates those microorganisms or bacteria derived from the microorganism *L. rhamnosus* CECT 30031 having a 16s rRNA sequence that is at least 99% identical to the 16s rRNA sequence of the *L. rhamnosus* strain of SEQ ID NO 1 of *L. rhamnosus* CECT 30031 and which retains the ability to reduce and/or improve the evolution of acne in an individual in need thereof of said *L. rhamnosus* CECT 30031.

The present invention also contemplates those microorganisms or bacteria derived from the microorganism *S. paraca* BEA_IDA_0074B (*Arthrospira platensis*

BEA_IDA_0074B), having a 16s rRNA sequence that is at least 95% identical to the 16s rRNA sequence of *S. paraca* BEA_IDA_0074B and which retains the ability to reduce and/or improve the evolution of acne in an individual in need thereof of *S. paraca* BEA_IDA_0074B.

Such derived bacteria may be part of, or totally or partially replacing, any of microorganisms *L. rhamnosus* CECT 30031 and/or *S. paraca* BEA_IDA_0074B, in any of the above probiotic compositions of the invention as long as they retain the ability to reduce and/or improve the evolution of acne in need thereof.

In the context of the present invention "retains the ability to reduce and/or improve the evolution of acne in an individual in need thereof" shall be understood as a significant improvement, in comparison to a subject treated with a placebo, of the GAGS (Global Acne Grading Score) index of at least 26%, together with an improvement of at least two categories of the AGSS (Acne Global Severeness Scale) index of 58% in the probiotic group in comparison with 33% in subjects in the placebo group, and optionally together with an improvement in at least 51% of the number of inflamed injuries compared with the results obtained with the treatment of a subject suffering from acne with oral antibiotics and/or a topical treatment with salicylic acid, azelaic acid and/or dapsone.

Examples of strains or microorganisms derived from strains comprised within any of the above-mentioned probiotic compositions of the invention may be mutants and genetically modified organisms which show variations in their genome compared to the genome of the strains of the invention from which they derived, but which do not affect the ability of strains to reduce and/or improve the evolution of acne in the individual. Strains derived from *L. rhamnosus* CECT 30031 and *S. paraca* BEA_IDA_0074B, can be naturally or intentionally produced by mutagenesis methods known in the art such as for example, but not limited to, the growth of the parent strain in the presence of mutagenic agents or stressors or by genetic engineering directed to the modification, deletion and/or insertion of specific genes. Thus, as indicated above, the present invention also contemplates genetically modified organisms derived from *L. rhamnosus* CECT 30031 and *S. paraca* BEA_IDA_0074B, that retain the ability to reduce and/or improve the evolution of acne in an individual and, therefore, to be used in the treatment of acne. Particular derived strains have a 16s rRNA sequence that is at least 95%, 96%, 97%, 98%, 99%, 99.5% or 99.9% identical to the 16s rRNA sequence of the parent strain (SEQ ID NO 1) and retain the ability of the parent strain to reduce and/or improve the evolution of acne in an individual in need thereof.

```
SEQ ID NO 1:
AGAGTTTGATCCTGGCTCAGGATGAACGCTGGCGGCGTGCC

TAATACATGCAAGTCGAACGAGTTCTGATTATTGAAAGGT

GCTTGCATCTTGATTTAATTTTGAACGAGTGGCGGACGGG

TGAGTAACACGTGGGTAACCTGCCCTTAAGTGGGGGATAA

CATTTGGAAACAGATGCTAATACCGCATAAATCCAAGAAC

CGCATGGTTCTTGGCTGAAAGATGGCGTAAGCTATCGCTT

TTGGATGGACCCGCGGCGTATTAGCTAGTTGGTGAGGTAA

CGGCTCACCAAGGCAATGATACGTAGCCGAACTGAGAGGT
```

```
                    -continued
TGATCGGCCACATTGGGACTGAGACACGGCCCAAACTCCT

ACGGGAGGCAGCAGTAGGGAATCTTCCACAATGGACGCAA

GTCTGATGGAGCAACGCCGCGTGAGTGAAGAAGGCTTTCG

GGTCGTAAAACTCTGTTGTTGGAGAAGAATGGTCGGCAGA

GTAACTGTTGTCGGCGTGACGGTATCCAACCAGAAAGCCA

CGGCTAACTACGTGCCAGCAGCCGCGGTAATACGTAGGTG

GCAAGCGTTATCCGGATTTATTGGGCGTAAAGCGAGCGCA

GGCGGTTTTTTAAGTCTGATGTGAAAGCCCTCGGCTTAAC

CGAGGAAGTGCATCGGAAACTGGAAAACTTGAGTGCAGAA

GAGGACAGTGGAACTCCATGTGTAGCGGTGAAATGCGTAG

ATATATGGAAGAACACCAGTGGCGAAGGCGGCTGTCTGGT

CTGTAACTGACGCTGAGGCTCGAAAGCATGGGTAGCGAAC

AGGATTAGATACCCTGGTAGTCCATGCCGTAAACGATGAA

TGCTAGGTGTTGGAGGGTTTCCGCCCTTCAGTGCCGCAGC

TAACGCATTAAGCATTCCGCCTGGGGAGTACGACCGCAAG

GTTGAAACTCAAAGGAATTGACGGGGGCCCGCACAAGCGG

TGGAGCATGTGGTTTAATTCGAAGCAACGCGAAGAACCTT

ACCAGGTCTTGACATCTTTTGATCACCTGAGAGATCGGGT

TTCCCCTTCGGGGGCAAAATGACAGGTGGTGCATGGTTGT

CGTCAGCTCGTGTCGTGAGATGTTGGGTTAAGTCCCGCAA

CGAGCGCAACCCTTATGACTAGTTGCCAGCATTTAGTTGG

GCACTCTAGTAAGACTGCCGGTGACAAACCGGAGGAAGGT

GGGGATGACGTCAAATCATCATGCCCCTTATGACCTGGGC

TACACACGTGCTACAATGGATGGTACAACGAGTTGCGAGA

CCGCGAGGTCAAGCTAATCTCTTAAAGCCATTCTCAGTTC

GGACTGTAGGCTGCAACTCGCCTACACGAAGTCGGAATCG

CTAGTAATCGCGGATCAGCACGCCGCGGTGAATACGTTCC

CGGGCCTTGTACACACCGCCCGTCACACCATGAGAGTTTG

TAACACCCGAAGCCGGTGGCGTAACCCTTTTAGGGAGCGA

GCCGTCTAAGGTGGGACAAATGATTAGGGTGAAGTCGTAA

CAAGGTAGCCGTAGGAGAACCTGCGGCTGGATCACCT
```

Furthermore, the present invention, also contemplates cellular components, metabolites and molecules secreted by the *L. rhamnosus* CECT 30031 and *S. paraca* BEA_IDA_0074B strains. as well as compositions comprising said components and uses thereof for the treatment and/or prevention of acne. The cellular components of bacteria could include components of the cell wall (such as, but not limited to, peptidoglycan), nucleic acids, membrane components and other, such as proteins, lipids and carbohydrates and combinations thereof (such as lipoproteins, glycolipids or glycoproteins). Metabolites include any molecule produced or modified by the bacterium or microalgae as a result of its metabolic activity during growth, its use in technological processes or during storage of the product (first probiotic composition of the invention). Examples of these metabolites include, but are not limited to, organic and inorganic acids, proteins, peptides, amino acids, enzymes, lipids, carbohydrates, lipoproteins, glycolipids, glycoproteins, vitamins, salts, minerals or nucleic acids. Secreted molecules include any molecule secreted or released to the outside by the bacterium during growth, its use in technological processes (for example, food processing or drugs) or during storage of the product. Examples of these molecules include, but are not limited to, organic and inorganic acids, proteins, peptides, amino acids, enzymes, lipids, carbohydrates, lipoproteins, glycolipids, glycoproteins, vitamins, salts, minerals or nucleic acids.

As understood by those skilled in the art, any of the probiotic compositions of the invention may be formulated for pharmaceutical administration, i.e., forming part of pharmaceutical products to be administered to the subject (either orally, topically, etc., preferably orally), and/or for food administration, i.e. forming part of the foods consumed in the subject's diet, thus being administered orally. Therefore, in a particular embodiment, any of the compositions or probiotic compositions of the invention can be a pharmaceutical composition (from hereinafter pharmaceutical composition of the invention) and/or a nutritional composition (from hereinafter nutritional composition of the invention). Such pharmaceutical compositions of the invention can thus be used in the treatment and/or prevention of diseases characterized by the overproduction of sebum, in particular those that block the pilosebaceous unit that form comedones. In particular, such pharmaceutical compositions of the invention are used in the prevention or treatment of acne, in particular of acne vulgaris, more particularly in the prevention or treatment of comedones. Comedones are the skin-coloured, small bumps (papules) frequently found on the forehead and chin of those with acne. A single lesion is a comedo. Open comedones are blackheads; black because of surface pigment (melanin), rather than dirt. Closed comedones are whiteheads; the follicle is completely blocked.

The pharmaceutical compositions of the invention thus comprise microorganisms *L. rhamnosus* CECT 30031 and/or *S. paraca* BEA_IDA_0074B (or strains derived therefrom as defined above) at any concentration and may additionally comprise one or more components or compounds having any biological, pharmacological and/or veterinary useful activity in the prevention and/or treatment of acne, in particular for the treatment or prevention of comedones. Such pharmaceutical compositions may further comprise one or more components which, upon administration to a subject, may further increase, enhance and/or promote the activity of the strains included in any of the probiotic compositions of the invention. As understood by one skilled in the art, the additional components or compounds must be compatible with the strains of any of the probiotic compositions of the invention. In the context of the present invention, the term "pharmaceutical composition" also encompasses veterinary compositions.

In a particular embodiment, the pharmaceutical composition of the invention further comprises a pharmaceutically acceptable carrier and/or excipient.

The term "excipient" refers to a substance that helps the absorption of any components or compounds of any of the probiotic compositions of the invention, namely, of strains of the invention, or stabilizes the components or compounds and/or assists the preparation of the pharmaceutical composition in the sense of giving it consistency or flavors to make it more pleasant. Thus, the excipients may have the function, by way of example but not limited thereto, of binding the components (for example, starches, sugars or cellulose), sweetening, colouring, protecting the active ingredient (for example, to insulate it from air and/or moisture), filling a pill, capsule or any other presentation or a disintegrating function to facilitate dissolution of the components, without excluding other excipients not listed in this paragraph. Therefore, the term "excipient" is defined as that material that included in the galenic forms, is added to the active ingredients or their associations to enable their preparation and stability, modify their organoleptic properties or determine the physico-chemical properties of the pharmaceutical composition and its bioavailability. The "pharmaceutically acceptable" excipient must allow the activity of components or compounds of the pharmaceutical composition, that is, be compatible with the strains of the invention.

The "galenic form" or "pharmaceutic form" is the configuration to which the active ingredients and excipients are adapted to provide the pharmaceutical composition or drug of the invention. It is defined by the combination of the form in which the pharmaceutical composition is presented by the manufacturer and the form in which it is administered.

The "vehicle" or "carrier" is particularly an inert substance. Carrier functions are to facilitate the incorporation of other components or compounds, allow better dosage and administration and/or give consistency and form to the pharmaceutical composition. Therefore, the carrier is a substance used in the drug to dilute any of the components or compounds of the pharmaceutical composition of the present invention to a given volume or weight; or that even without diluting these components or compounds, it is able to allow better dosage and administration and/or give consistency and form to the drug. When the presentation is liquid, the pharmaceutically acceptable carrier is the diluent. The carrier can be natural or unnatural. Examples of pharmaceutically acceptable carriers include, without being limited thereto, water, salt solutions, alcohol, vegetable oils, polyethylene glycols, gelatin, lactose, starch, amylose, magnesium stearate, talc, surfactants, silicic acid, viscous paraffin, perfume oil, monoglycerides and diglycerides of fatty acids, fatty acid esters petroetrals, hydroxymethylcellulose, polyvinylpyrrolidone and the like.

Furthermore, the excipient and the carrier must be pharmacologically acceptable, i.e., the excipient and the carrier are permitted and evaluated so as not to cause damage to the subject to whom it is administered.

In each case the presentation of the pharmaceutical composition will be adapted to the type of administration used. Thus, the composition may be presented in the form of solutions or any other form of clinically permissible administration and in a therapeutically effective amount. The pharmaceutical composition can be thus formulated into solid, semisolid or liquid preparations, such as tablets, capsules, powders (such as those derived from lyophilization (freeze-drying) or air-drying), granules, solutions, suppositories, gels or microspheres. In a particular embodiment, the pharmaceutical composition is formulated for administration in liquid form or in solid form. In an embodiment, the composition is in form of gelatin capsules.

In another particular embodiment, the solid formulation is selected from the group consisting of tablets, lozenges, sweets, chewable tablets, chewing gums, capsules, sachets, powders, granules, coated particles or coated tablets, tablet, pills, troches, gastro-resistant tablets and capsules and dispersible strips and films.

In another particular embodiment, the liquid formulation is selected from the group consisting of oral solutions, suspensions, emulsions and syrups.

Likewise, various systems are known that can be used for sustained-release administration of any of the probiotic, pharmaceutical or nutritional compositions of the invention, including, for example, the encapsulation in liposomes, microbubbles, microparticles or microcapsules and the like. The suitable sustained-release forms as well as materials and methods for their preparation are well known in the state of the art. Thus, the orally administrable form of any of the probiotic compositions of the invention is in a sustained-release form further comprising at least one coating or matrix. The sustained release coating or matrix includes, without limitation, natural semisynthetic or synthetic polymers, water-insoluble or modified, waxes, fats, fatty alcohols, fatty acids, natural, semisynthetic or synthetic plasticizers or a combination of two or more of the same. Enteric coatings can be applied using conventional processes known to those skilled in the art.

In addition to what has been described above, the present invention also encompasses the possibility that any of the probiotic compositions, probiotic pharmaceutical or nutritional compositions of the present invention (as reflected in any aspect or embodiment described throughout the present specification) may be administered to a subject together with other components or compounds, although these are not part of the probiotic compositions, probiotic pharmaceutical or nutritional compositions of the present invention. In this sense, in the event that the composition of the invention is formulated as a nutritional composition, said nutritional composition may be a food or be incorporated into a food or food product intended for both human and animal consumption. Thus, in a particular embodiment, the nutritional composition is selected from between a food (which may be a food for specific nutritional purposes or medicinal food) and a nutritional supplement.

In the present invention, the term "nutritional composition" refers to that food, which regardless of providing nutrients to the subject who consumes it, beneficially affects one or more functions of the body, so as to provide better health and wellness. In the present invention, said nutritional composition is intended to ease, reduce, treat and/or prevent acne.

The term "supplement", synonymous with any of the terms "dietary supplement", "nutritional supplement", "food supplement", or "alimentary supplement" or "alimentary complement" refers to products or preparations whose purpose is to supplement the normal diet consisting of sources of concentrated nutrients or other substances with a nutritional or physiological effect. In the present invention, the "substance" which has a nutritional or physiological effect on the individual when the alimentary complement is ingested are the microorganisms *L. rhamnosus* CECT 30031 and/or *Spirulina paraca* BEA_IDA_0074B, which are part of any of the compositions of the present invention. The food supplement may be in single or combined form and be marketed in dosage form, i.e. in capsules, pills, tablets and other similar forms, sachets of powder, ampoules of liquids and drop dispensing bottles and other similar forms of liquids and powders designed to be taken in a single amount.

There is a wide range of nutrients and other elements that may be present in alimentary complements including, among others, vitamins, minerals, amino acids, essential fatty acids, fibre, enzymes, plants and plant extracts. Since their role is to complement the supply of nutrients in a diet, they should not be used as a substitute for a balanced diet and intake should not exceed the daily dose expressly recommended by the doctor or nutritionist. The probiotic composition can also be part of the so-called "food for special groups", i.e. foods that meet specific nutritional needs.

Examples of foods that may comprise the compositions or probiotic compositions of the invention (microorganisms *L. rhamnosus* CECT 30031 and/or *Spirulina paraca* BEA_IDA_0074B (or strains derived therefrom)), include, but are not limited to, feed, dairy products, vegetable products, meat products, snacks, chocolates, drinks, baby food, cereals, fried foods, industrial bakery products and biscuits. Examples of milk products include, but are not limited to, products derived from fermented milk (for example, but not limited to, yogurt or cheese) or non-fermented milk (for example, but not limited to, ice cream, butter, margarine or whey). The vegetable product is, for example, but not limited to, a cereal in any form of presentation, fermented (for example, soy yogurt, oat yogurt, etc.) or unfermented, and a snack. The beverage may be, but is not limited to, non-fermented milk. In a particular embodiment, the food product or food is selected from the group consisting of fruit or vegetable juices, ice cream, infant formula, milk, yogurt, cheese, fermented milk, powdered milk, lyophilized or air-dried products (suitable for reconstitution with a liquid vehicle), cereals, baked goods, milk-based products, meat products and beverages.

As understood by those skilled in the art, any of the compositions or probiotic compositions of the invention may be formulated as forming part of personal care products or cosmetic products to be administered to the subject e.g. topically. Therefore, in a particular embodiment, any of the compositions or probiotic compositions of the invention can be a personal care product or a cosmetic product.

Non-limiting examples of personal care products include bar soap, liquid soap (e.g., hand soap), hand sanitizer (including rinse off and leave-on alcohol based and aqueous-based hand disinfectants), cotton swabs and pads, shaving cream, talcum powder, toiled paper, preoperative skin disinfectant, wet paper, cleansing wipes, disinfecting wipes, body wash, acne treatment products, antifungal diaper rash cream, antifungal skin cream, shampoo, conditioner, cosmetics deodorant, antimicrobial creams, body lotion, hand cream, topical cream, aftershave lotion, skin toner, oral hygiene products, and sunscreen lotion. The compositions of the invention may also be applied to wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. In one particular embodiment, the personal care product is a topical cream or gel.

Additionally, any of the compositions, probiotic compositions, pharmaceutical or nutritional compositions of the present invention (as reflected in any aspect or embodiment described throughout the present specification), may comprise other microorganisms in addition to *L. rhamnosus* CECT 30031 and/or *Spirulina paraca* BEA_IDA_0074B. Thus, in a particular embodiment, any of the compositions, probiotic, pharmaceutical or nutritional compositions of the present invention (as reflected in any aspect or embodiment described throughout the present specification) may further comprise one or more microorganism selected, among others, from the following group: *Lactobacillus* sp., *Streptococcus* sp., *Bifidobacterium* sp., *Saccharomyces* sp., and combinations thereof.

In another particular embodiment, any of the compositions of the invention are administered to a subject through the diet.

In another particular embodiment, any of the compositions of the invention are administered to a subject via oral administration.

As understood by one skilled in the art, the microorganisms *L. rhamnosus* CECT 30031 and/or *Spirulina paraca* BEA_IDA_0074B (or any microorganisms derived therefrom) have to be present in the probiotic, pharmaceutical or nutritional compositions of the present invention (as reflected in any aspect or embodiment described throughout the present specification) in an effective amount, particularly in a therapeutically effective amount, so that they can exert their effect of easing, reducing, treating and/or preventing acne, in particular of acne vulgaris, more particularly in easing, reducing, treating and/or preventing comedones. In the present invention "effective amount" or "therapeutically effective amount" is that amount of the component or compound of the probiotic, pharmaceutical or nutritional compositions of the present invention, which when administered to a subject, is sufficient to produce the desired effect. Said component or compound of the probiotic, pharmaceutical or nutritional compositions of the present invention (as reflected in any aspect or embodiment described throughout the present specification), refers to the microorganisms *L. rhamnosus* CECT 30031 and/or *Spirulina paraca* BEA_IDA_0074B. The therapeutically effective amount will vary depending on, for example, age, body weight, general health, sex and diet of the subject, as well as according to the mode and time of administration, excretion rate or drug combination, among other factors.

In another particular embodiment, the total concentration of microorganisms *L. rhamnosus* CECT 30031 and/or *Spirulina paraca* BEA_IDA_0074B (or any microorganisms derived therefrom), in any of the compositions of the invention is between $10^3$ and $10^{12}$ cfu, particularly approximately $10^9$ cfu. In another particular embodiment, the dose of administration of microorganisms *L. rhamnosus* CECT 30031 and/or *Spirulina paraca* BEA_IDA_0074B (or any microorganisms derived therefrom), in the composition is between $10^6$ and $10^{12}$ cfu/day, particularly $10^9$ cfu/day, and in another even more particular embodiment, the administration regime is at least once daily, in particular twice daily, and more in particular, three times a day, one with each food intake (breakfast, lunch and dinner).

In another particular embodiment of any of the probiotic pharmaceutical or nutritional compositions of the present invention (as reflected in any aspect or embodiment described throughout the present specification), the concentration of *L. rhamnosus* CECT 30031 is at least thirty percent (30%) with respect to the total concentration of microorganisms present in the composition, particularly at least 31%, 32%, 33%, 34% or 35% relative to the total concentration of microorganisms present in any of the compositions of the invention. In another even more particular embodiment, the concentration of *L. rhamnosus* CECT 30031 is at least 35%, 40%, 45%, 50%, 55%, 60%, 65%, 70%, 75%, 80%, 85%, 90%, 91%, 92%, 93%, 94%, 95%, 96%, 97%, 98%, or 99%, preferably at least 60%, 65%, 70%, 75% or 80%, most preferred at least 85%, 90%, 91%, 92%, 93%, 94%, 95%, 96% with respect to the total amount of microorganisms present in any of the compositions of the invention.

In another embodiment of present invention, any of the probiotic pharmaceutical or nutritional compositions comprise between $10^3$ to $10^{12}$ colony forming units (cfu), more preferred at least about $10^6$ cfu, most preferred at least about $10^9$ cfu of *L. rhamnosus* CECT 30031.

In a preferred embodiment of present invention, the concentration of *L. rhamnosus* CECT 30031 is between 90% to 95% with respect to the total amount of microorganisms present in the compositions of present invention. Preferably this concentration of *L. rhamnosus* CECT 30031 provides for an amount of between $10^3$ to $10^{12}$ colony forming units (cfu), more preferred at least about $10^6$ cfu, most preferred about $10^9$ cfu of *L. rhamnosus* CECT 30031 in said compositions.

In one embodiment of the present invention the amount of *S. paraca* BEA_IDA_0074B is at least 5%, 6%, 7%, 8%, 9%, 10%, 11%, 12%, 13%, 14%, 15%, 16%, 17%, 18%, 19% or 20% of the total dry weight of microorganisms present in the compositions of present invention.

In a further embodiment the compositions of the present invention comprise between 2 mg to 20 mg, preferably 3 mg to 15 mg, most preferred 5 mg to 12 mg (dry weight) of *S. paraca* BEA_IDA_0074B.

In a further embodiment any of the compositions of present invention comprise at least 0.5 mg of phycocyanin, said phycocyanin preferably being derived from the *S. paraca* BEA_IDA_0074B comprised in said composition.

In the context of present invention it is to be understood that about 10% of the total dry weight of *S. paraca* BEA_IDA_0074B is comprised of phycocyanin produced by the strain itself. Therefore, any of the compositions of present invention preferably contain at least 5 mg (dry weight) of *S. paraca* BEA_IDA_0074B leading to an amount of at least 0.5 mg (dry weight) of phycocyanin in said composition.

In a preferred embodiment of any of the probiotic pharmaceutical or nutritional compositions of the present invention the compositions are provided in daily dosage units, each daily dosage unit comprising at least 0.5 mg (dry weight) of phycocyanin derived from *S. paraca* BEA_IDA_0074B and at least about $10^6$, preferably about $10^9$ cfu of *L. rhamnosus* CECT 30031.

In yet a further embodiment of the present invention the probiotic pharmaceutical or nutritional compositions of the present invention further comprise at least one bulking agent and/or at least one anti-caking agent and/or at least one coating agent and optionally at least one opacifier.

Preferably said at least one bulking agent of present invention is maltodextrin and/or said at least one coating agent of present invention is gelatin and/or said at least one opacifier is titanium dioxide.

The at least one anti-caking agent of present invention can be selected from the group consisting of magnesium stearate, calcium stearate, silica, silicates, such as sodium or calcium silicate, talc, flour, starch, or combinations thereof.

In a preferred embodiment the bulking agent is maltodextrin, the anti-caking agent is magnesium stearate, the coating agent is gelatin and the opacifier is titanium dioxide.

Specifically, any of the probiotic compositions, probiotic pharmaceutical or nutritional compositions of the present invention (as reflected in any aspect or embodiment described throughout the present specification), are used in a method of treating or preventing acne, in particular of acne vulgaris, more particularly in a method of easing, reducing, treating and/or preventing comedones, in a subject or individual, comprising, particularly orally, administering to said subject or individual, an effective amount of the composition thereby treating or preventing said acne or comedones. As already indicated previously, it is noted that orally suitable liquid preparations to be used for the compositions of the present invention, may be in the form of, for example, aqueous or oily suspensions, solutions, emulsions, syrups or elixirs, or may be presented as a dry product, such as a lyophilized (freeze-dried) or air-dried product, for constitution with water or other suitable liquid vehicles before use. Such liquid preparations may contain conventional additives such as suspending agents, emulsifying agents, non-aqueous vehicles (which may include edible oils), or preservatives. In one further embodiment, the method of the invention for treating acne in a subject, may further comprise the step of sequentially, subsequently or simultaneously administering to said subject an effective amount of an additional agent, such as isotrenitoin, salicylic acid, witch hazel or Benzoyl peroxide, topical or oral retinoid, spironolactone, an oral contraceptive, azaleic acid, glycolic acid, topical or oral antibiotics, sulfa-based anti-biotics, spf/sunblock, moisturizers or a combination thereof in other embodiments. A person skilled in the art will readily recognize that the components of any treatment composition may be adjusted and optimized based on the symptoms exhibited by the subject, their severity and potential synergistic or antagonistic interactions among the components of such treatment, without exceeding the scope of the invention.

In one further embodiment, the methods and compositions of the invention are used as a supplementary or adjuvant treatment for acne, wherein an effective amount of any of the compositions of the present invention, as defined herein, are typically administered orally, either singly or in combination (simultaneously, sequentially or subsequently) with another compound or compounds such isotrenitoin, salicylic acid, witch hazel or Benzoyl peroxide, topical or oral retinoid, spironolactone, an oral contraceptive, azaleic acid, glycolic acid, topical or oral antibiotics, sulfa-based antibiotics, spf/sunblock, or moisturizers. In particular, with antibiotics such as but not limited to topical or oral antibiotics, sulfa-based antibiotics; or hormonal agents for the treatment of acne such as oral contraceptives or antiandrogens. The administration can be carried out in one embodiment, in single unit dosage form with continuous therapy or in another embodiment, in single dose therapy ad libitum. Other embodiments of administration are effective for treating the acne conditions. In other embodiments, any of the compositions of the invention are used when relief of symptoms is specifically required, or, in one embodiment, imminent. Lastly, any of the compositions of the invention may be further used in another embodiment, as a continuous or prophylactic treatment.

Throughout the description and claims the word "comprise" and its variants are not intended to exclude other technical characteristics, additives, components or steps. For those skilled in the art, other objects, advantages and characteristics of the invention will become apparent in part from the description and partly from the practice of the invention. The following examples and figures are provided by way of illustration and are not intended to limit the scope of the present invention.

EXAMPLES

Example 1. Probiotic Blend Study

Study Products: Probiotic Blend and Placebo

The probiotic blend used in this first example is a Maltodextrin-based formula named Bths-03 containing a mixture of two strains comprising at least $1 \times 10^9$ cfu (colony forming units) per gram.

In the following table, details on the composition and function of the treatment used during this pilot trial are included (Table 2):

TABLE 2

| INGREDIENTS | FUNCTION |
|---|---|
| Maltodextrin (360 mg) | Bulking agent |
| Probiotic blend: | Probiotic |
| Strain 1. *L. rhamnosus* CECT 30031 (95 mg) | |
| Strain 2. *S. paraca* BEA_IDA_0074B (5 mg) | |
| Gelatin | Capsule coating agent |
| Magnesium stearate (10 mg) | Anti-caking agent |
| Titanium dioxide (E-171) | Capsule opacifier |

The composition above were in the form of white gelatin capsules (in particular 30 capsules per product) each of 570 mg and each having dimensions of 21.7 mm±0.5%.

The placebo was produced with the same format as the experimental drug containing 30 mg of tapioca maltodextrin per capsule.

Method of Producing the Studied Blended Product

A lyophile from the probiotic *L. rhamnosus* and that from spirulina were mixed prior to encapsulation. Mixing was done in a clean room at low temperature to preserve the viability of the probiotic strains. Once mixed, the capsules were encapsulated.

Dose and Information about How to Take the Product 1 capsule a day for 12 weeks.

The capsules were of a suitable size to be swallowed easily.

The capsules could be easily opened and were suitable for dispersing its contents in a glass of water.

Indication Studied

Improvement of acne symptoms in adolescents and adults.

Study Design

A 12-week, randomized, double-blind, placebo-controlled study using a product with selected probiotics in the active arm.

Population Groups

Adolescents and adults with moderate acne between 12 and 30 years for both sexes, assigned randomly in a 1:1 ratio in two study groups: experimental (probiotic) and placebo.

Objectives of the Study

Primary Objective

To determine if the consumption of the probiotic mixture Bths-03 had a beneficial effect and decreased the symptoms of acne in adolescents and adults.

Secondary Objectives

Evaluating the adherence of patients to the treatment and their experience with it. Determining the safety of the study treatment.

Research Plan and Method

Design of the Study

Double-blind, placebo-controlled pilot trial, on the efficacy of the orally-administered probiotic Bths-03 in patients aged 12-30 years suffering from Moderate Acne in a 12-week trial treatment.

Criteria on Patients Selection

In the present study adolescents and adults with moderate acne of both genders between 12 and 30 years old participated, not including healthy patients. The subjects participating in the study had to meet all the inclusion criteria and none of the exclusion criteria detailed herein below:

Inclusion Criteria

1. Signature of informed consent by the patient (and their legal guardian in case of being a minor) in accordance with the legislation on clinical trials.

2. Age between 12 and 30 years.

3. Moderate acne according to the AGSS scale (Acne Global Severeness Scale) and/or GAGS (Global Acne Grading System).

Exclusion Criteria

1. Contraindication of any of the components of the product under study.
2. Topical or systemic use of antifungals and antibiotics in the previous 2 weeks.
3. Consumption of probiotics in the previous 2 months.
4. Use of systemic retinoids in the previous 6 months.

Variables in the Study

Main Variable

GAGS index score (Global Acne Grading System) at the start, 6 and 12 weeks of treatment.

Secondary Variables

AGSS scale (Acne Global Severeness Scale)

Number of acne lesions evaluated through the taking of digital photographs.

Perception and subjective evaluation of the patient.

Study of the adherence of patients to treatment.

Observation of the possible adverse effects derived from the treatment.

Structure and Study Outcome

The total duration of the intervention period in the study of each patient was 12 weeks during which the patient was administered either study product Bths-03 or placebo. The study was structured in three visits, in which the patient attended the consultation: initial visit (0 weeks), intermediate visit (6 weeks) and final visit (12 weeks). The following diagram indicates what each of the study visits included (Table 3):

TABLE 3

| | VISIT | | |
|---|---|---|---|
| | 0/1 | 2 | 3 |
| | WEEK | | |
| | 0 | 6 | 12 |
| Information sheet | X | | |
| Informed consent | X | | |
| Inclusion and exclusion criteria | X | | |
| Randomization | X | | |
| Clinical history of patient | X | | |
| Treatment delivery | X | X | |
| GAGS (Global Acne Grading System) | X | X | X |
| AGSS (Acne Global Severity Scale) | X | X | X |
| Number of lesions | X | X | X |
| Subjective evaluation of patient | X | X | X |
| Adherence to treatment | | X | X |
| Side effects | | X | X |

Collection and Interpretation of Adverse Effects

Adverse events were collected in visits 2 and 3 of the study, according to the information provided by the patients.

Likewise, there was a procedure to be followed in case of a serious adverse events (AAG), but this event did not occur during the development of the study. According to this study, AAG was considered to be one that, at any dose, produced:

death, immediately threatened the subject's life, lead to hospitalization or its prolongation, produced persistent or significant disability or incapacity (inability to perform correctly their vital functions), lead to an anomaly or congenital malformation of birth, in the case of women, AAG will also be considered pregnancy, and those suspicions of an adverse event that were considered important and clinically relevant, even if they did not meet the above criteria.

Statistical Analysis

Number of Patients Included in the Study

A sample size of 25 patients was estimated to be included in the study. When comparing the two treatment groups, the main factors that were taken into consideration for the sample calculation were:

1. The size of the difference in the variables to be measured between the two groups so that it can detect it.
2. How much variability existed in the interest factor to analyse.
3. The "p" value that was expected to be used as a criterion of statistical significance (alpha risk).
4. The security to detect a statistically significant difference, assuming that this difference exists (beta risk).

Randomization Method

The clinical study was a double-blind and randomized, that is, both the researcher and the patient were unaware of the product (placebo or treatment) that each participating patient was receiving.

In order to maintain this randomization and not generating biases in the assessment of the participating patients, the allocation of each patient to their treatment was made using randomization tables and random codes were assigned to each product to avoid its identification. These tables were in charge of a responsible person outside the study with which the researcher contacted each time he had to include a new patient.

Evaluation and Analysis of Results

Demographic Data and Other Baseline Characteristics

In this study, the data of the subjects were collected in a Data Collection Notebook (CRD), they were entered in a database generated with the statistical program SPSS v22.

The management of the clinical data was carried out in accordance with the rules and procedures for data purification that proceed to ensure the integrity of the data, for example, eliminating errors and inconsistencies of the same. The terms for adverse events and concomitant medications were coded according to the Medical Dictionary for Regulatory Activities (MedDRA).

To test if there was a statistically significant difference between the means of the variables associated with each treatment group, the Student t test was used. In cases where the condition of normality was clearly violated, the non-parametric Mann-Whitney U test was used.

Security Analysis

The adverse events were analyzed according to their number, their severity and their relationship with the product under study in each intervention group.

Missing, Absent or Atypical Data

10% follow-up loss rate was estimated in the study design. All patients who completed the scheduled visits to the study (protocol) were included in the final data analysis (assessable subjects) while all other patients were excluded from the analysis, not being replaced by new patients once they were withdrawn from the study.

Results

Characteristics of the Population to Study

In total, 25 patients who met the inclusion criteria and none of the exclusion criteria, were assessed during the study. In the table included below (Table 4), the general characteristics of the total of this population included in the study are shown.

TABLE 4

| MAIN VARIABLES | SCORE/VALUE |
| --- | --- |
| SEX (FEMALE) N(%) | 13(52%) |
| AGE (YEARS) | 20.42 |
| WEIGHT (KG) | 71.42 |
| HEIGHT (CM) | 171 |
| ALLERGICAL N(%) | 9(36%) |
| GACS INDEX | 23.20 |
| AGSS INDEX | 2.71 |
| INFLAMED LESIONS | 20.04 |
| TOTAL SKIN LESIONS | 50.33 |
| SUBJECTIVE ASSESSMENT SCORE | 8.75 |

It is noted that during the development of the study, a total of 32 patients were evaluated, of which finally 7 were not included because they did not meet the inclusion and exclusion criteria defined in the protocol and/or because they declined to participate in the study. From the total number of patients, the 25 remaining and participating patients were randomized at the time of their inclusion, assigning them to one of the treatment groups (probiotic or placebo). In this process the patients were distributed homogeneously, since 12 patients entered the probiotic group, and 13 to the placebo group. During the study, a total of 1 patient (in the placebo) decided to leave voluntarily and/or contact was lost during the intervention. The consort diagram used in this study is illustrated in FIG. 1.

When analysing the data of these variables in the baseline, proper randomization was achieved, as there were no significant differences in the characteristics between the two groups. These data are illustrated in the following Table 5:

TABLE 5

| Main Variables | Probiotic (n = 12) | PLACEBO (n = 12) |
| --- | --- | --- |
| Sex (female) n(%) | 6 | 7 |
| Age (years) | 20.08 | 20.75 |
| Weight (kg) | 70.33 | 72.50 |
| Height (cm) | 170.17 | 171.83 |
| Allergical n(%) | 4 | 5 |
| GACS index | 23.58 | 22.83 |
| AGSS index | Category 1 | Category 1 |
| | 0 | 0 |
| | Category 2 | Category 2 |
| | 3 | 4 |
| | Category 3 | Category 3 |
| | 9 | 8 |
| Inflamed lesions | 19.70 | 20.42 |
| Total skin lesions | 48.80 | 51.80 |
| Subjective assessment score | 11.5 | 12.4 |

Efficacy Analysis

Main Variable. GAGS (Global Acne Grading System) Index

Figure 2:
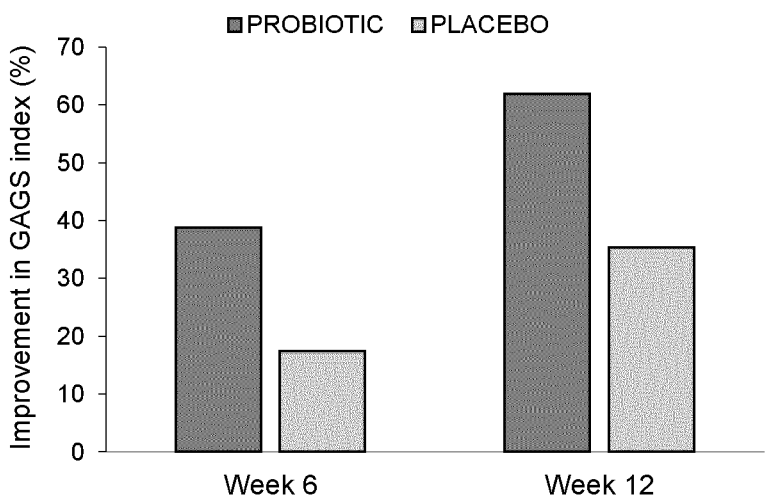
FIG. 2. This figure shows the evaluation of the GAGS (Global Acne Grading System) index at 6 and 12 weeks for the Probiotic blend study of example 1.

The data of the main variable is shown in FIG. 2. It is noted that the average reduction of the GAGS index (main outcome) was in relative terms of 61% in the probiotic group and 24% in the placebo group. The differences at the end of the study compared with the value shows were of 61.8% in the probiotic group and of 35.4% in the placebo group.

Secondary Variables

AGSS (Acne Global Severity Scale) Index

Figure 3:
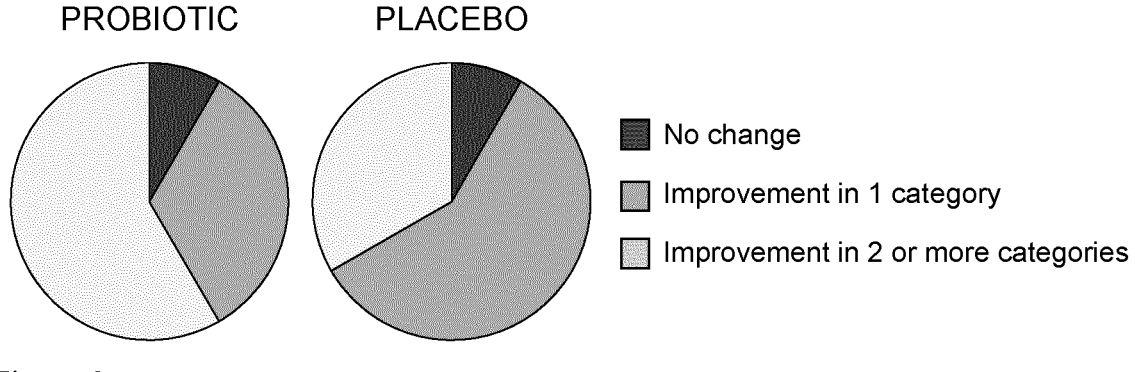
FIG. 3. This figure shows the evaluation of the AGSS (Acne Global Severity Scale) index at 6 and 12 weeks for the Probiotic blend study of example 1.

The data of this secondary variable is shown in FIG. 3. The differences at the end of the study in the variable "percentage of patients improving two or more categories" was 58% in the probiotic group and 33% in the placebo group. Intragroup differences were statistically significant in the probiotic group but were not significant in the placebo one.

Number of Inflamed Acne Lesions

Figure 4:
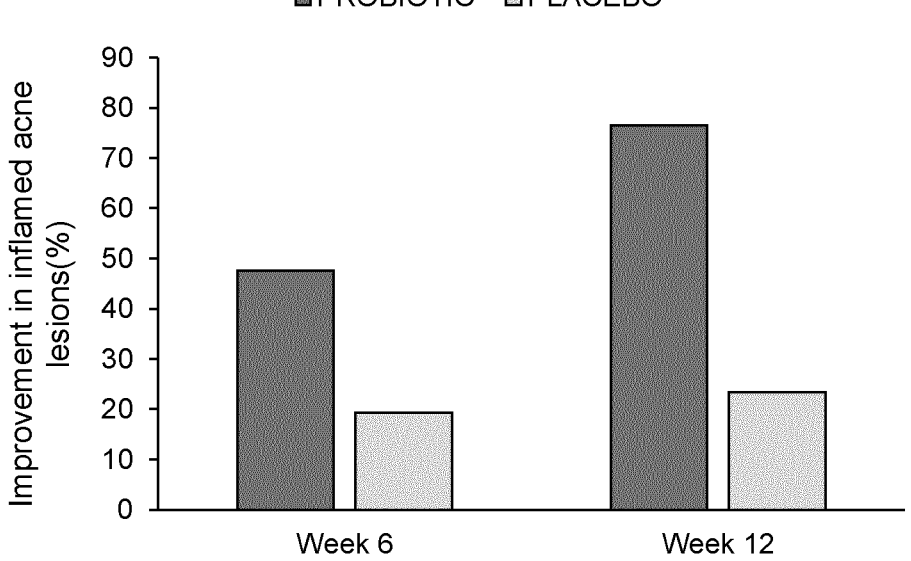
FIG. 4. This figure shows the evaluation of the number of inflamed acne lesions at 6 and 12 weeks for the Probiotic blend study of example 1.

This variable was evaluated through high-resolution digital photographs. For this variable, there was an improvement of 47.58% in the probiotic group compared to an improvement of 19.37% in the placebo group in the intermediate analysis of the study established six weeks after the intervention. Data related to this variable at the end of the study is illustrated in the FIG. 4. The differences at the end of the study were 76.5% in the probiotic group and 23.38% in the placebo group. The difference between groups was clinically and statistically significant (p<0.05).

Perception and Subjective Evaluation of the Patient.

In this variable, there was an improvement of 11.67% in the probiotic group compared to an improvement of 3.33% in the placebo group in the intermediate analysis of the study established six weeks after the intervention.

Figure 5:
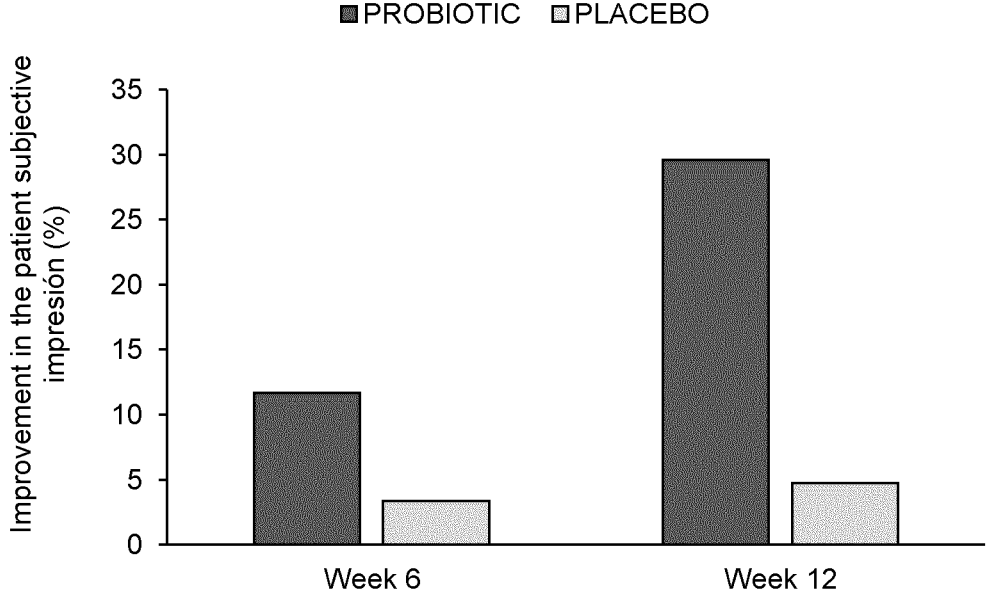
FIG. 5. This figure shows the evaluation of the perception and subjective evaluation of the patient at 6 and 12 weeks for the Probiotic blend study of example 1.

The differences at the end of the study were 29.58% in the probiotic group and 4.75% in the placebo group. The data of this variable at the end of the study is represented in FIG. 5.

Security Analysis and Side Effects

Number of events, severity and relationship with the product. The number of adverse events was very low, all of them not attributable to the intervention product. The final preparation of the product was well tolerated with a treatment adherence of 82.5% in probiotic group and 86.67 in placebo group in the intermediate analysis of the study established six weeks after the intervention. The data of this variable at the end of the study was 86.25% in the probiotic group and 86.67% in the placebo group.

Example 2. Three-Branch Study

Each of strains L. rhamnosus CECT 30031 and S. paraca BEA_IDA_0074B were evaluated separately for the treatment of acne vulgaris. For such purpose a small pilot study was performed with five patients in each one of a three-branch study using L. rhamnosus CECT 30031, S. paraca BEA_IDA_0074B or CECT 30031 and S. paraca BEA_IDA_0074B. In particular, a total of 15 volunteers with acne vulgaris were selected and randomized in a 1:1:1 ratio, in each one of the following three intervention treatments:

1. L. rhamnosus CECT 30031, one capsule per day containing 100 mg of the probiotic strain with a total dose of 10E9 cfu/dose.
2. S. paraca BEA_IDA_0074B, one capsule per day containing a total of 100 mg of the probiotic strain with a total dose of 10E9 cfu/dose.
3. The combination of the two probiotic strains at the same doses that were used individually.

The intervention lasted 12 weeks and during such intervention the patients were evaluated at the start of the treatment, and one month, two months and finally three months after the end of the intervention. In each of the visits, the response to treatment was evaluated using activity indices.

The results of the three-branch study are summarized herein below:

These results include for each one of the variables, differences between the value that was obtained at the end of the intervention study with the value obtained in the beginning, before the treatment began. The results for each one of the three interventional groups are here included:

Strain 1. *L. rhamnosus* CECT 30031 (when Used Individually)

IL-10: increase during the study 23% from baseline value.
Lipopolysaccharides in blood: decreased 14%.
DNA in blood decreased 2%.
GAGS improvement 24%.
AGSS improvement in 1 out of 5 cases.
Inflammatory spots decreased in 23% cases.

Strain 2. *Spirulina paraca* (when Used Individually)

IL-10: increase during the study 11% from baseline value.
Lipopolysaccharides in blood: decreased 6%.
DNA in blood decreased 3%.
GAGS improvement 13%.
AGSS no improvement.
Inflammatory lesions decreased in 11%.

Blend Using *L. rhamnosus* CECT 30031 and *Spirulina paraca* (when Used in Combination)

IL-10: increase during the study 36% from baseline value.
Lipopolysaccharides in blood: decreased 42%.
DNA in blood decreased 68%.
GAGS improvement 56%.
AGSS improvement in three out of five cases
Inflammatory lesions decreased in 57%

In conclusion, this study illustrates how the effect is potentiated and thus significantly improved when both strains are used in combination compared with the effect of each of the separate strains.

Example 3. Comparative Analysis

For this example, a probiotic composition comprising the *S. paraca* BEA_IDA_0074B strain was specifically compared with a probiotic composition containing the known strain (Strain 1. *L. rhamnosus* SP1) disclosed in: "Fabbrocini G, Bertona M, Picazo Ó, Pareja-Galeano H, Monfrecola G, Emanuele E. Supplementation with *Lactobacillus rhamnosus* SP1 normalises skin expression of genes implicated in insulin signaling and improves adult acne. Benef Microbes. 2016; 7 (5): 625-630. doi: 10.3920/BM2016.0089". Such known strain was considered in the prior art as effective for the treatment of acne vulgaris (see Table 1 above). For this study, the design, intervention product and results are summarized herein below.

Variables in the Study

GAGS index score (Global Acne Grading System) at the start and 12 weeks of treatment.
AGSS scale (Acne Global Severeness Scale) at the start and 12 weeks of treatment.
Number of inflamed acne lesions at the start and 12 weeks of treatment, evaluated through the taking of digital photographs.

Structure and Study Outcome

The total duration of the intervention period in the study of each patient was 12 weeks during which the patient was administered either study product: one group of 5 patients received *L. rhamnosus* sp1; another 5 patients in the second group received *S. paraca* BEA_IDA_0074B and finally the third group of 5 patients received a mixture of *L. rhamnosus* sp1 and *S. paraca* BEA_IDA_0074B. The study was structured in two visits, in which the patient attended the consultation: initial visit (0 weeks), and final visit (12 weeks).

Results

Main Variable

GAGS (Global Acne Grading System) Index

It is noted that the average reduction (The difference at the end of the study compared with the value before the treatment started) in the GAGS index value was in relative terms of 15% in the group receiving *L. rhamnosus* SP1. This reduction was 12% in the *S. paraca* BEA_IDA_0074B group of patients and 12% in the group of 5 patients receiving the mixture composition of *L. rhamnosus* SP1 and *S. paraca* BEA_IDA_0074B.

Secondary Variables

AGSS (Acne Global Severity Scale) Index

The number of patients that improved during the treatment (comparing results from the beginning with those at the end of the study), was 1 out 5 (20%) in the *L. rhamnosus* SP1 group; 0 of 5 (0%) in the *S. paraca* BEA_IDA_0074B group and finally 1 of 5 (20%) in the mixture of *L. rhamnosus* and *S. paraca* BEA_IDA_0074B group.

Number of Inflamed Acne Lesions

This variable was evaluated through high-resolution digital photographs. For this variable, there was a reduction of the number of inflamed lesions of 17% (compared the number of lesions at the end of the study with the value at the beginning of the study) in the group of *L. rhamnosus* sp1. The reduction was 9% in the *S. paraca* BEA_IDA_0074B group and 12% in the group of patients that received the mixture of *L. rhamnosus* and *S. paraca* BEA_IDA_0047B.

The invention claimed is:

1. A probiotic composition comprising a lyophilized powder of:
    a. *Lactobacillus rhamnosus* strain deposited under the Budapest treaty in the Spanish Type culture Collection (CECT) under accession number CECT 30031;
    b. *Arthrospira platensis* (*Spirulina* paraca) strain deposited in the Banco Español de Algas under accession number BEA_IDA_0074B; and
    c. at least one bulking agent, at least one anti-caking agent, and/or at least on coating agent.

2. The probiotic composition according to claim 1, wherein said composition is formulated for administration in liquid form or in solid form for oral administration.

3. The probiotic composition according to claim 1, wherein said composition is a pharmaceutical composition comprising pharmaceutically acceptable excipients or a nutritional composition or nutritional supplement.

4. The probiotic composition according to claim 3, wherein said composition is in the form of (a) a formulation selected from the group consisting of tablets, lozenges, sweets, chewing gum, capsules, sachets, powders, granules, dispersible strips, and films, or (b) a liquid formulation selected from the group consisting of oral solutions, suspensions, emulsions and syrups.

5. A method of easing, reducing, treating and/or preventing acne in a subject in need thereof, comprising administering to said subject an effective amount of a probiotic composition comprising:

(a) *Lactobacillus rhamnosus* strain deposited under the Budapest treaty in the Spanish Type culture Collection (CECT) under accession number CECT 30031; and
    (b) *Arthrospira platensis* (*Spirulina* paraca) strain deposited in the Banco Español de Algas under accession number BEA_IDA_0074B;
thereby treating said acne.

6. The method according to claim 5, wherein the probiotic composition is orally administered to the subject.

7. The method according to claim 6, wherein at least one additional compound is administered in an effective amount for treating acne to said subject.

8. The method according to claim 5, wherein the acne is selected from the group consisting of Acne vulgaris, Acne rosacea, Acne conglobate, Acne fulminans, Gram-negative folliculitis, and Pyoderma Faciale.

9. The method according to claim 8, wherein the acne is Acne vulgaris.

10. A method of easing, reducing, treating and/or preventing acne, in particular of acne vulgaris in a subject in need thereof, comprising administering to said subject an effective amount of a probiotic composition comprising *Arthrospira platensis* (*Spirulina paraca*) strain deposited in the Banco Español de Algas under accession number BEA_IDA_0074B.

11. A method of easing, reducing, treating and/or preventing acne in a subject in need thereof, comprising administering to said subject an effective amount of a probiotic composition comprising *Lactobacillus rhamnosus* strain deposited under the Budapest treaty in the Spanish Type culture Collection (CECT) under accession number CECT 30031.

12. The method according to claim 10, wherein the acne is selected from the group consisting of Acne vulgaris, Acne rosacea, Acne conglobate, Acne fulminans, Gram-negative folliculitis, and Pyoderma Faciale.

13. The method according to claim 10, wherein the probiotic composition is administered orally to the subject in need thereof.

14. The method according to claim 6, wherein the acne is selected from the group consisting of Acne vulgaris, Acne rosacea, Acne conglobate, Acne fulminans, Gram-negative folliculitis, and Pyoderma Faciale.

15. The method according to claim 14, wherein the acne is Acne vulgaris.

16. The method according to claim 11, wherein the acne is selected from the group consisting of Acne vulgaris, Acne rosacea, Acne conglobate, Acne fulminans, Gram-negative folliculitis, and Pyoderma Faciale.

17. The method according to claim 11, wherein the probiotic composition is administered orally to the subject in need thereof.

* * * * *

```
                    SEQUENCE LISTING

<160> NUMBER OF SEQ ID NOS: 1

<210> SEQ ID NO 1
<211> LENGTH: 1558
<212> TYPE: RNA
<213> ORGANISM: Lactobacillus rhamnosus
<220> FEATURE:
<223> OTHER INFORMATION: 16s rRNA sequence

<400> SEQUENCE: 1
agagtttgat cctggctcag gatgaacgct ggcggcgtgc ctaatacatg caagtcgaac      60
gagttctgat tattgaaagg tgcttgcatc ttgatttaat tttgaacgag tggcggacgg     120
gtgagtaaca cgtgggtaac ctgcccttaa gtgggggata acatttggaa acagatgcta     180
ataccgcata aatccaagaa ccgcatggtt cttggctgaa agatggcgta agctatcgct     240
tttggatgga cccgcggcgt attagctagt tggtgaggta acggctcacc aaggcaatga     300
```

-continued

```
tacgtagccg aactgagagg ttgatcggcc acattgggac tgagacacgg cccaaactcc      360
tacgggaggc agcagtaggg aatcttccac aatggacgca agtctgatgg agcaacgccg      420
cgtgagtgaa gaaggctttc gggtcgtaaa actctgttgt tggagaagaa tggtcggcag      480
agtaactgtt gtcggcgtga cggtatccaa ccagaaagcc acggctaact acgtgccagc      540
agccgcggta atacgtaggt ggcaagcgtt atccggattt attgggcgta aagcgagcgc      600
aggcggtttt ttaagtctga tgtgaaagcc ctcggcttaa ccgaggaagt gcatcggaaa      660
ctggaaaact tgagtgcaga agaggacagt ggaactccat gtgtagcggt gaaatgcgta      720
gatatatgga agaacaccag tggcgaaggc ggctgtctgg tctgtaactg acgctgaggc      780
tcgaaagcat gggtagcgaa caggattaga taccctggta gtccatgccg taaacgatga      840
atgctaggtg ttggagggtt tccgcccttc agtgccgcag ctaacgcatt aagcattccg      900
cctggggagt acgaccgcaa ggttgaaact caaaggaatt gacgggggcc cgcacaagcg      960
gtggagcatg tggtttaatt cgaagcaacg cgaagaacct taccaggtct tgacatcttt     1020
tgatcacctg agagatcggg tttccccttc ggggcaaaa tgacaggtgg tgcatggttg     1080
tcgtcagctc gtgtcgtgag atgttgggtt aagtcccgca acgagcgcaa cccttatgac     1140
tagttgccag catttagttg ggcactctag taagactgcc ggtgacaaac cggaggaagg     1200
tggggatgac gtcaaatcat catgcccctt atgacctggg ctacacacgt gctacaatgg     1260
atggtacaac gagttgcgag accgcgaggt caagctaatc tcttaaagcc attctcagtt     1320
cggactgtag gctgcaactc gcctacacga agtcggaatc gctagtaatc gcggatcagc     1380
acgccgcggt gaatacgttc ccgggccttg tacacaccgc ccgtcacacc atgagagttt     1440
gtaacacccg aagccggtgg cgtaaccctt ttagggagcg agccgtctaa ggtgggacaa     1500
atgattaggg tgaagtcgta acaaggtagc cgtaggagaa cctgcggctg gatcacct       1558
```